(12) United States Patent
Pianca

(10) Patent No.: US 9,387,319 B2
(45) Date of Patent: *Jul. 12, 2016

(54) SYSTEM FOR PERMANENT ELECTRODE PLACEMENT UTILIZING MICROELECTRODE RECORDING METHODS

(75) Inventor: Anne M. Pianca, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 126 days.

This patent is subject to a terminal disclaimer.

(21) Appl. No.: 13/196,402

(22) Filed: Aug. 2, 2011

(65) Prior Publication Data

US 2011/0288619 A1    Nov. 24, 2011

Related U.S. Application Data

(63) Continuation of application No. 11/670,598, filed on Feb. 2, 2007, now Pat. No. 8,010,200, which is a continuation of application No. 10/459,068, filed on Jun. 11, 2003, now Pat. No. 7,177,701, which is a continuation-in-part of application No. 10/035,745, filed on Dec. 28, 2001, now Pat. No. 7,033,326.

(60) Provisional application No. 60/258,767, filed on Dec. 29, 2000, provisional application No. 60/388,871, filed on Jun. 13, 2002.

(51) Int. Cl.
*A61N 1/00*    (2006.01)
*A61N 1/05*    (2006.01)
*A61B 5/04*    (2006.01)

(52) U.S. Cl.
CPC .......... *A61N 1/0529* (2013.01); *A61B 5/04001* (2013.01); *A61N 1/0539* (2013.01); *Y10S 439/909* (2013.01)

(58) Field of Classification Search
CPC ............. A61B 5/04001; A61N 1/0529; A61N 1/0539; Y10S 439/909
USPC ........................................................ 607/116
See application file for complete search history.

(56) References Cited

U.S. PATENT DOCUMENTS

| | | |
|---|---|---|
| 3,147,750 A | 9/1964 | Fry |
| 3,826,244 A | 7/1974 | Salcman et al. |
| 4,471,777 A | 9/1984 | McCorkle, Jr. |

(Continued)

FOREIGN PATENT DOCUMENTS

| | | |
|---|---|---|
| EP | 1 062 973 A1 | 12/2000 |
| WO | WO 99/36122 A1 | 7/1999 |

*Primary Examiner* — George Manuel
(74) *Attorney, Agent, or Firm* — Lowe Graham Jones PLLC; Bruce E. Black

(57) ABSTRACT

A lead stimulation/recording system is provided, which is a combination of a permanent DBS stimulating lead and a recording microelectrode. The DBS lead has a lumen extending from the proximal to the distal end of the lead, the lumen having an opening on each end of the lead. The microelectrode is configured and dimensioned to be insertable into the DBS lead from either the distal or proximal opening of the DBS lead, thereby permitting the microelectrode to be placed before, concurrently with, or after placement of the DBS lead. In addition, the system may be used with known microelectrode recording systems and methods of inserting the electrodes, such as the five-at-a-time method, the dual-microdrive method, or the single microdrive method.

16 Claims, 10 Drawing Sheets

(56) References Cited

U.S. PATENT DOCUMENTS

| | | | |
|---|---|---|---|
| 4,565,200 A | | 1/1986 | Cosman |
| 4,886,065 A | | 12/1989 | Collins, Jr. |
| 5,006,122 A | | 4/1991 | Wyatt et al. |
| 5,116,345 A | | 5/1992 | Jewell et al. |
| 5,398,683 A | * | 3/1995 | Edwards et al. ............ 600/374 |
| 5,549,936 A | | 8/1996 | Tohma et al. |
| 5,618,287 A | | 4/1997 | Fogarty et al. |
| 5,743,870 A | * | 4/1998 | Edwards ..................... 604/22 |
| 5,752,937 A | | 5/1998 | Otten et al. |
| 5,755,766 A | | 5/1998 | Chastain et al. |
| 5,843,148 A | | 12/1998 | Gijsbers et al. |
| 5,925,073 A | | 7/1999 | Chastain et al. |
| 6,011,996 A | | 1/2000 | Gielen et al. |
| 6,026,567 A | | 2/2000 | Swoyer et al. |
| 6,050,954 A | | 4/2000 | Mittermeier |
| 6,066,165 A | | 5/2000 | Racz |
| 6,181,971 B1 | | 1/2001 | Doan |
| 6,301,492 B1 | | 10/2001 | Zonenshayn |
| 6,343,226 B1 | | 1/2002 | Sunde et al. |
| 6,356,792 B1 | | 3/2002 | Errico et al. |
| 6,413,263 B1 | | 7/2002 | Lobdill et al. |
| 6,416,520 B1 | | 7/2002 | Kynast et al. |
| 6,456,889 B2 | | 9/2002 | Pianca et al. |
| 6,546,289 B2 | | 4/2003 | Knapp |
| 6,572,624 B2 | | 6/2003 | U et al. |
| 6,799,074 B1 | | 9/2004 | Thomas et al. |
| 7,177,701 B1 | | 2/2007 | Pianca |
| 7,285,118 B1 | | 10/2007 | Lozano |
| 2001/0027336 A1 | | 10/2001 | Gielen et al. |

* cited by examiner

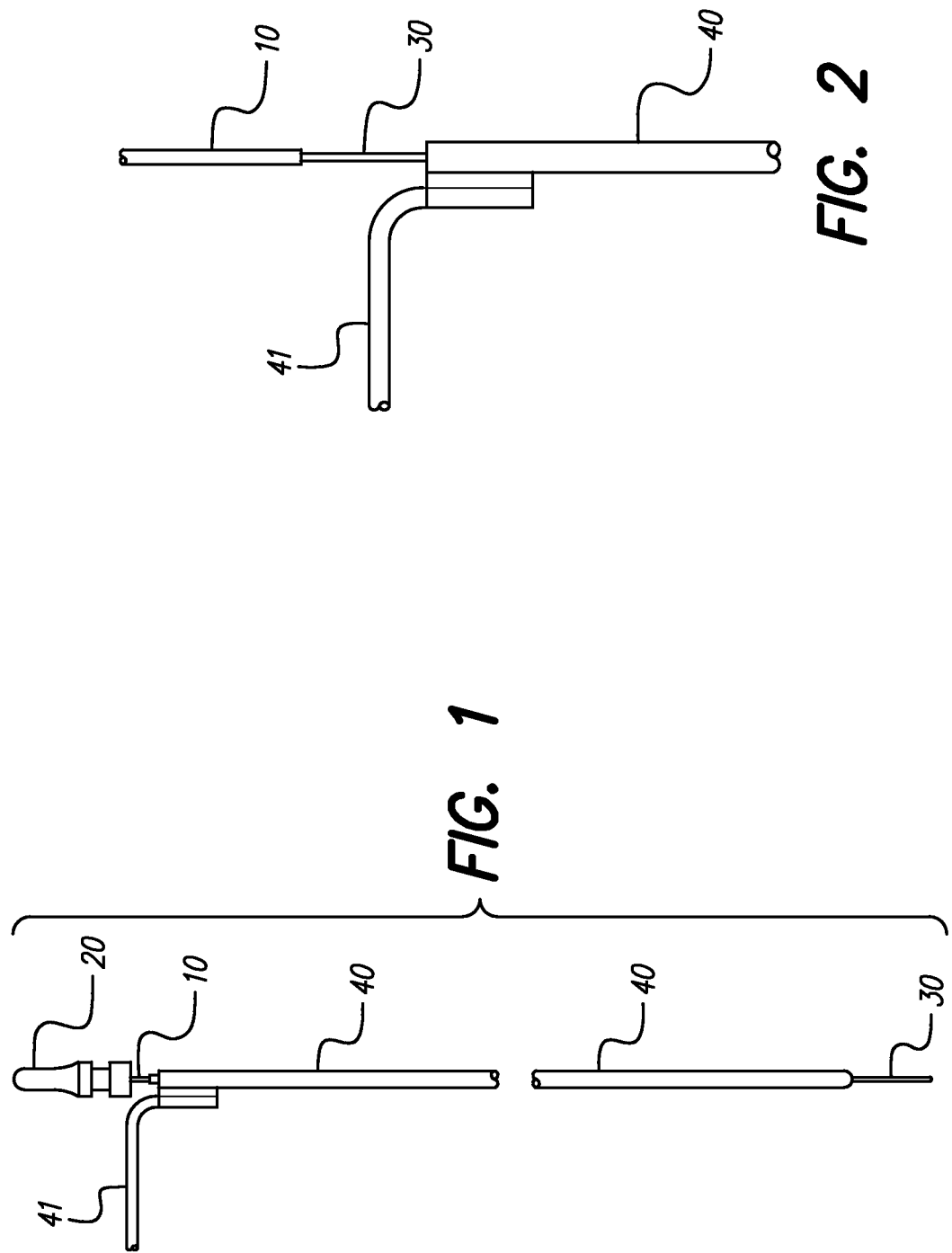

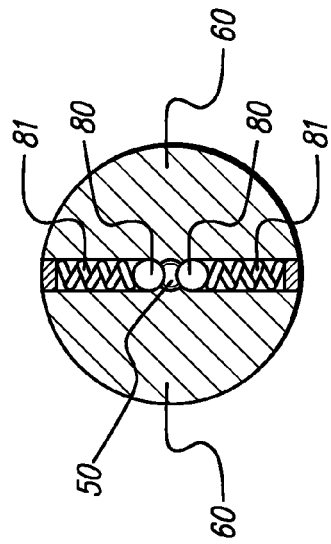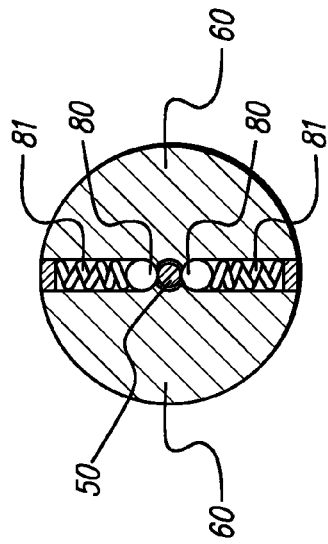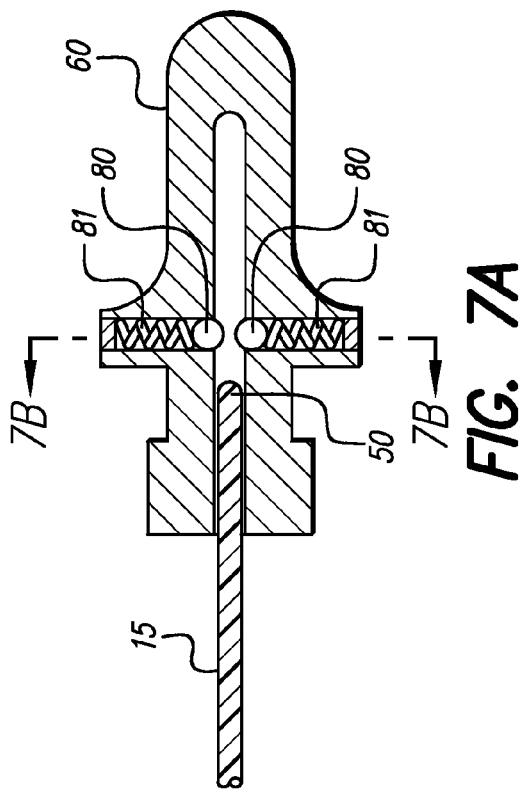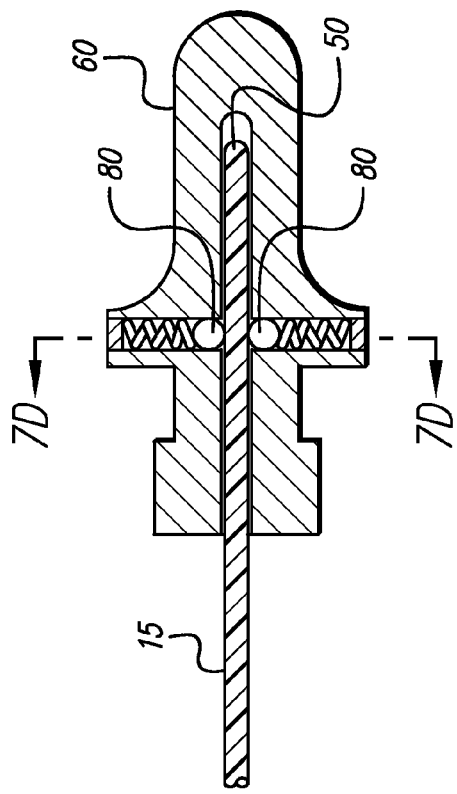

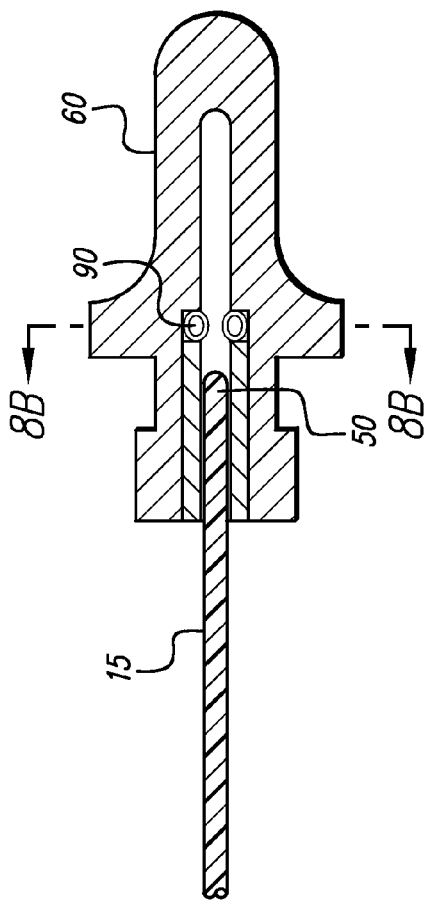
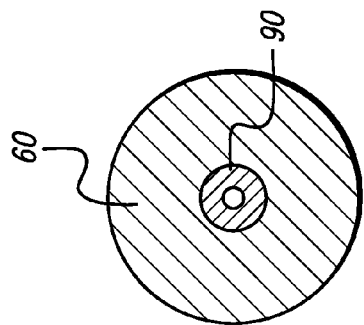
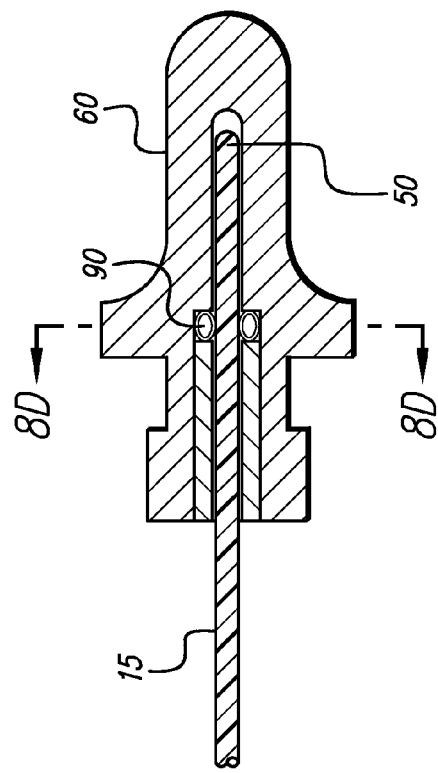
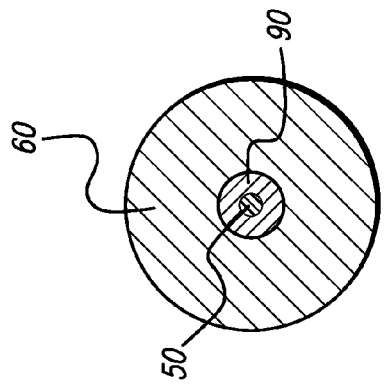

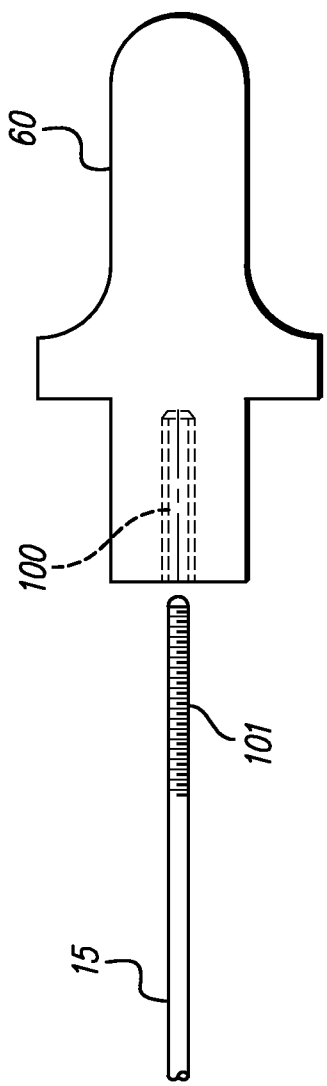
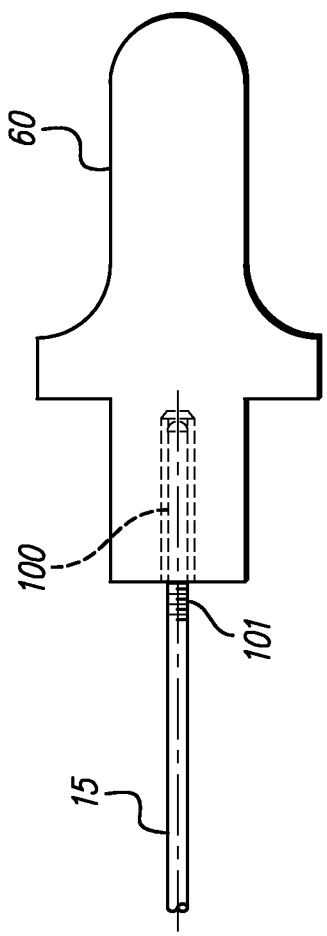

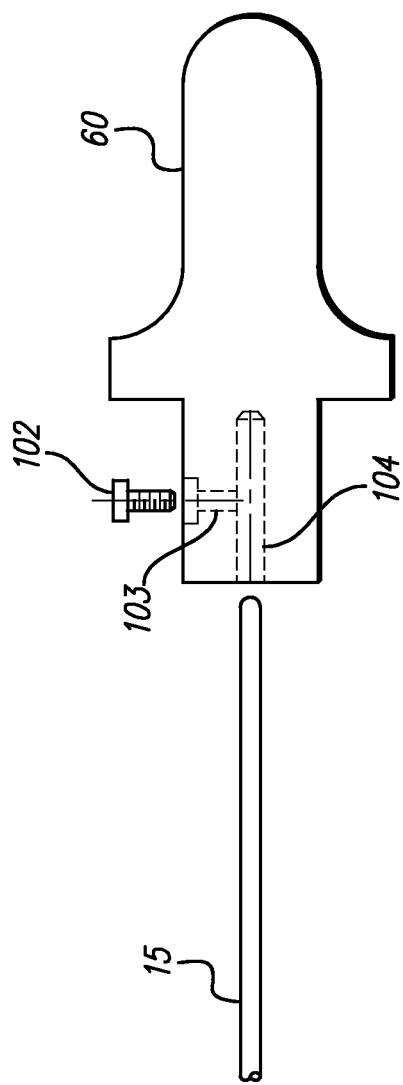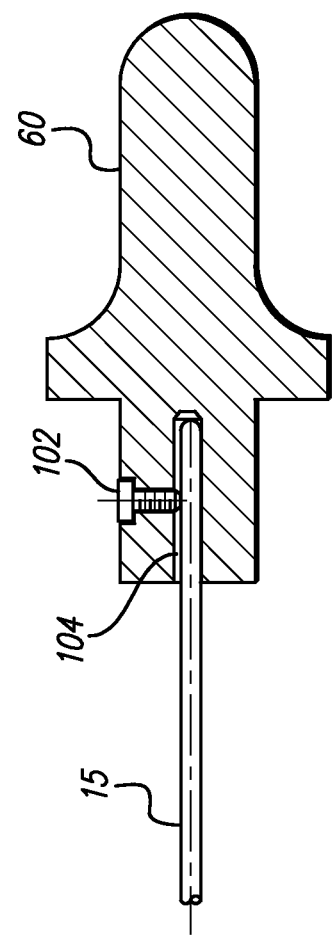

SYSTEM FOR PERMANENT ELECTRODE PLACEMENT UTILIZING MICROELECTRODE RECORDING METHODS

The present application is a Continuation of application Ser. No. 11/670,598, filed Feb. 2, 2007, which application is a Continuation of application Ser. No. 10/459,068, filed Jun. 11, 2003, issued as U.S. Pat. No. 7,177,701 on Feb. 13, 2007; which application is a Continuation-In-Part of U.S. patent application Ser. No. 10/035,745, filed Dec. 28, 2001, issued as U.S. Pat. No. 7,033,326 on Apr. 25, 2006; which application claims the benefit of U.S. Provisional Patent Application Ser. No. 60/258,767, filed Dec. 29, 2000, which applications and patents are incorporated by reference.

In addition, application Ser. No. 10/459,068 claims the benefit of U.S. Provisional Patent Application Ser. No. 60/388,871, filed Jun. 13, 2002, which application is also incorporated herein by reference.

BACKGROUND OF THE INVENTION

The present invention relates to medical leads and microelectrode recording systems used for functional neurosurgical procedures.

Deep brain stimulation (DBS) is being increasingly accepted as a viable treatment modality. In particular DBS applied to the thalamus for treatment of tremor was approved by the FDA in 1997. Subsequently, other diseases, such as Parkinson's Disease, dystonia, and chronic pain, among others, have been identified as candidates for treatment with deep brain stimulation.

The term "stylet," as used in this disclosure, is an implement inserted into the lumen of a stimulating lead to stiffen the lead and to facilitate its insertion into the target tissue. The term "rod," as used in this disclosure, is an implement that is placed inside a cannula to provide support to the cannula, while it is inserted into target tissue. The term "microelectrode" refers to a recording electrode which can be essentially a wire which has at least the distal portion of the wire uninsulated to receive electrical signals from the recorded tissue. The term "macroelectrode" will refer to a stimulating electrode and parts connected to the electrode, which macroelectrode is intended as a temporary test electrode to perform macrostimulation. Macrostimulation involves stimulating many cells at once. The term "lead," as used hereinafter, will specifically refer only to a chronically implantable stimulation electrode, including parts connected to the electrode. The electrode portion of the lead is that portion which is in electrical contact with tissue. The term "tract" refers to an individual pathway formed in tissue, for example, by inserting a microelectrode, a macroelectrode, a lead or an associated cannula into that tissue.

Implantation of a lead for deep brain stimulation generally involves the following preliminary steps: (a) anatomical mapping and (b) physiological mapping. Anatomical mapping involves mapping segments of an individual's brain anatomy using non-invasive imaging techniques such as magnetic resonance imaging (MRI) and computed axial tomography (CAT) scans. Physiological mapping involves localizing the brain site to be stimulated. Step (b) can be further divided into: (i) preliminarily identifying a promising brain site by recording individual cell activity with a microelectrode and (ii) confirming physiological stimulation efficacy of that site by performing a test stimulation with a macroelectrode.

Microelectrode recording is generally performed with a small diameter electrode with a relatively small surface area optimal for recording cell activity. The microelectrode may be essentially a wire which has at least the distal portion uninsulated to receive electrical signals. The rest of the body or wire of the microelectrode may be insulated. The microelectrode functions as a probe to locate a promising brain site. Since a number of attempts may be required to locate the precise target site, it is desirable that the microelectrode be as small as possible to minimize trauma when the microelectrode is placed into the brain, in some cases, multiple times.

Once a brain site has been identified, a macroelectrode is used to test that the applied stimulation has the intended therapeutic effect. A macroelectrode is a temporary stimulating electrode and is not intended to be chronically implanted. Because macrostimulation involves stimulating many cells at once, an optimal electrode for macrostimulation requires a larger surface area compared to a microelectrode, which merely records electrical activity from a single cell or a few cells. For this reason, the conductive electrode surface of a macroelectrode is generally larger than the conductive electrode surface of a microelectrode. The macroelectrode can be retraced into the same brain site identified with microelectrode cell recordings.

Test stimulation with the macroelectrode may need to be performed in a number of tracts in order to localize the site which provides the proper physiological effect. Because the macroelectrode may need to be repeatedly inserted into the brain, the macroelectrode must be durable, stiff and resistant to buckling. The macroelectrode can be made from a sterilizable material.

Once macrostimulation confirms that stimulation at the brain site provides the intended physiological effect, the macroelectrode is withdrawn from the brain and a DBS lead is permanently implanted at the exact site.

Keeping in mind the above general steps, a conventional procedure for carrying out DBS may involve the following detailed steps: (1) place a stereotactic frame on the subject, which stereotactic frame is a device temporarily mounted on the head to assist in guiding the lead system into the brain; (2) perform MRI or equivalent imaging of the subject with the stereotactic frame; (3) identify a theoretical target using a planning software; (4) place the subject with the stereotactic frame in a head rest; (5) using scalp clips, cut the subject's skin flap in the head, exposing the working surface area of the cranium; (6) place the stereotactic arc with target coordinate settings and identify the location on skull for creation of a burr hole; (7) remove the arc and drill a burr hole in the patient's skull; (8) place the base of the lead anchor; and (9) with the microelectrode recording drive attached, and with an appropriate stereotactic frame adaptor inserted into the instrument guide, place the stereotactic arc.

Next, (10) advance a microelectrode cannula and an insertion rod into the brain until they are approximately 25 mm above the target; (11) remove the insertion rod, leaving the cannula in place; (12) insert a recording microelectrode such that the tip of the microelectrode is flush with the tip of the microelectrode cannula; (13) connect the connector pin of the recording microelectrode to a microelectrode recording system; (14) starting approximately 25 mm above the target, advance the microelectrode into a recording tract at the specified rate using the microdrive; and (15) if the target is identified, proceed to step 16. If the target is not identified, proceed with the following: (17) using the recording results and pre-operative imaging, (a) determine a new set of coordinates for the theoretical target; (b) disconnect the recording microelectrode from the microelectrode recording system; (c) remove the recording microelectrode cannula and recording microelectrode; and (d) adjust the coordinates of the stereotactic frame. Then, continue at step 10, above.

Next, (16) remove the recording microelectrode cannula and recording microelectrode; (17) insert a macroelectrode insertion cannula and rod until they are approximately 25 mm above the target; (18) remove the insertion rod, leaving the macroelectrode insertion cannula in place; (19) insert a stimulating macroelectrode, and advance it to the target stimulation site identified by the recording microelectrode; (20) using macrostimulation, simulate the stimulation of the chronic DBS lead to ensure proper physiological response; (21) remove the macroelectrode and cannula; (22) insert a DBS lead insertion cannula and an insertion rod, and advance both to approximately 25 mm above the stimulation site; (23) remove the insertion rod; (24) insert a DBS lead, with stylet, through the insertion cannula, and advance the lead/stylet to the stimulation site; (25) electrically connect the lead to a trial stimulator; and (26) perform the desired stimulation and measurements using any one or combination of four electrodes on the DBS lead.

Next, (27) if the results are favorable, proceed to step 28. If the results are not favorable, proceed with the following: (a) using the macrostimulation results and microelectrode recording results, as well as pre-operative imaging, determine a new set of coordinates for the theoretical target; (b) remove the lead and stylet; (c) remove the insertion cannula; (d) adjust the coordinates of the stereotactic frame; and (e) continue at step 10, above.

Next, (28) remove the stylet, followed by the insertion cannula; (29) using macrostimulation, verify that micro-dislodgement of the DBS lead has not occurred; and, finally, (30) lock the DBS lead in the lead anchor.

Some physicians might use additional steps, fewer steps, or perform the steps in a different order.

There are a number of commercially available microelectrode recording ("MER") systems used for deep brain stimulation. Such a system includes apparatuses for holding the microelectrodes in place and electronics that connect to the microelectrodes to enable cell recordings. MER systems are sold by Alpha Omega Engineering (Nazareth, Israel), Axon (Union City, Calif.), Atlanta Research Group (Atlanta, Ga.), and Microrecording Consultants (Pasadena, Calif.). The Alpha Omega and Axon systems appear to be among the most popular with functional neurosurgeons. None of these companies manufacture their own microelectrodes, although they may provide a microelectrode as part of the MER system package. The Fred Haer Corporation (FHC) markets a popular microelectrode which is sometimes provided in the MER system package.

The Alpha Omega Engineering MER system permits the neurosurgeon to simultaneously record "five-electrodes-at-a-time" recordings. In this approach all five of the microelectrodes are advanced into the brain at the same time and at the same speed. This presents obvious advantages. The set-up time may be proportionately cut, since the chance of locating a good stimulation site theoretically increases by five times. A disadvantage presented is that because the microelectrodes are placed relatively close to each other, two of these electrodes could "capture" a blood vessel between the electrodes, puncturing the vessel and possibly leading to intracranial bleeding. In contrast, when a single microelectrode is used, the blood vessel can often escape injury because the vessel can deflect away from the microelectrode or vice-versa. Thus, some neurosurgeons choose to use the Alpha Omega MER system with only a single microdrive, advancing one microelectrode at a time until a suitable placement site is found. Other neurosurgeons have used the Alpha Omega system with two independent microdrives, which provides the flexibility of recording independently from two tracts.

Other neurosurgeons use the Axon system, which can manually advance only one microelectrode at time. Some neurosurgeons average 4 to 5 microelectrode recording tracts to identify a suitable brain site. Other neurosurgeons only record from one recording tract, which cuts surgery duration, but which may not locate an optimal stimulation site. Without optimal electrode placement, the DBS lead may need to be stimulated at higher currents, which can cause the device battery to be drained more quickly. In addition, use of higher currents can increase the risk of undesirable side effects such as dysarthria (slurred speech) and abulia (an abnormal inability to make decisions or to act).

Each of these MER systems apply the conventional surgical procedure of using the microelectrode to find the target brain site, withdrawing the microelectrode, then placing a macroelectrode, followed by placing a DBS lead or alternatively, placing a DBS lead directly without using a macroelectrode. These conventional surgical procedures are far from ideal. The number of steps lengthen the surgical procedure and increase the risk for post-operative infection. In addition, having to retrace the microelectrode pathway and the macroelectrode pathway to place the DBS lead substantially increases the chances for misalignment and misplacement because each of these steps require use of a separate introduction cannula. Moreover, the use of at least three cannulas in the procedure can increase surgical duration and operative risk, simply from the number of objects inserted into the brain. In addition, retracing the pathway of the microelectrode and the macroelectrode as preliminary steps to placing the permanent DBS lead is fraught with misalignment/misplacement problems because the introduction cannulas may not trace the exact pathways desired. When there is a missed placement of a DBS lead, the DBS lead and stylet may have to be scrapped.

Accordingly, there is a need for a DBS lead/microelectrode system which is compatible with the available MER systems and the various methods of employing these recording systems, which DBS lead/microelectrode system eliminates surgical steps and reduces surgical duration, reduces operative risk, and improves the accuracy of placing the permanent stimulation DBS lead to provide optimal physiological therapy.

SUMMARY OF THE INVENTION

The present invention addresses the above and other needs by providing a DBS lead/microelectrode system which is compatible with available MER systems and a wide variety of recording techniques currently used by neurosurgeons, including "five-at-a-time," two independent microdrives, and single tract, multiple insertion methods.

In one aspect of the present invention, a system for recording and stimulating excitable tissue is provided comprising a stimulation lead and a microelectrode. The stimulating lead may have a lumen along its axial length. The lumen has two openings, a first opening at the proximal end of the lead and a second opening at the distal end of the lead. The microelectrode is configured and dimensioned to be completely passable through the lumen of the lead, commencing from either the first opening or the second opening of the lead.

In another embodiment, the system may comprise: a stimulating lead, a microelectrode, and a removable connector which can be attached and detached to the proximal end of the microelectrode. The microelectrode is configured and dimensioned to be completely passable through the lumen of the stimulating lead, commencing from either a first opening or a second opening of the stimulating lead.

In yet another embodiment, the above system may further include a locking mechanism incorporated into the connector. The locking mechanism on the connector may be a threaded connection, a clip connection, a set screw connection, a spring-loaded connection, a ball bearing connection, a Bal Seal connection, a collet connection or an interference fit.

In each system embodiment, the stimulation lead may contain a conductor coil that defines an inner, axial lumen. The stimulation lead may have, at its proximal end, a connector portion that is angled from the remainder of the lead. This connector angle helps to divert the lead connection away from the remainder of the lead and prevents tangling with the microelectrode. The stimulation lead may have an array of electrodes placed on the distal portion of the lead in an in-line placement.

In another aspect of the invention, there is provided a method of placing a DBS stimulating lead and inserting a microelectrode that eliminates procedural steps and thus reduces critical operating time. Each embodiment of the method commonly shares the feature that the microelectrode may be inserted and fully passed through the lumen of the stimulating lead, commencing at the lead's distal or proximal end. The embodiments of the method include: (1) placing the microelectrode into tissue first and placing the DBS stimulating lead over the microelectrode, (2) concurrently placing the microelectrode/DBS stimulating lead into a target tissue, or (3) placing the DBS stimulating lead into the target tissue first and then inserting the microelectrode into the lumen of the DBS stimulating lead. The flexibility of the various method embodiments can increase the accuracy of placing a DBS lead and microelectrode near the target neurons and thereby improve treatment efficacy and conserve the device battery life.

BRIEF DESCRIPTION OF THE DRAWINGS

The above and other aspects, features and advantages of the present invention will be more apparent from the following particular description thereof, presented in conjunction with the following drawings wherein:

FIG. 1 shows a view of a conventional microelectrode having a permanently attached connector with the microelectrode inserted into an Advanced Bionics® DBS lead;

FIG. 2 shows a view of the proximal end of the Advanced Bionics DBS lead and the distal end of a conventional microelectrode;

FIG. 7A shows, in accordance with the present invention, a longitudinal, cross-sectional view of a connector and a microelectrode having a ball bearing connection, with the connector in an unlocked position;

FIG. 7B shows a cross-sectional view of the connector and microelectrode depicted in FIG. 7A along lines 7B-7B;

FIG. 7C shows a longitudinal, cross-sectional view of the connector and microelectrode shown in FIG. 7A, with the connector in a locked position;

FIG. 7D shows a cross-sectional view of the connector and microelectrode depicted in FIG. 7C along lines 7D-7D;

FIG. 8A shows, in accordance with the present invention, a longitudinal, cross-sectional view of a microelectrode and a connector having a Bal Seal connection, with the connector in an unlocked position;

FIG. 8B shows a cross-sectional view of the connector and microelectrode depicted in FIG. 8A along lines 8B-8B;

FIG. 8C shows a longitudinal, cross-sectional view of the microelectrode and connector shown in FIG. 8A, with the connector in a locked position;

FIG. 8D shows a cross-sectional view of the connector and microelectrode depicted in FIG. 8C along lines 8D-8D;

FIG. 9A shows a side view of a proximal end of a microelectrode 15 and a removable connector with a threaded connection;

FIG. 9B shows a side view of the removable connector 60 and microelectrode 15 of FIG. 9A, with the proximal end of the microelectrode screwed into the removable connector;

FIG. 10A shows a side view of a proximal end of a microelectrode 15 and a removable connector 60 with a set screw and a set screw hole;

FIG. 10B shows a side cross-sectional view of the removable connector 60 and the microelectrode 15 of FIG. 10A with the proximal end of the microelectrode placed into the removable connector and the set screw screwed into place to mechanically secure the proximal end of the microelectrode with the connector;

Corresponding reference characters indicate corresponding components throughout the several views of the drawings.

DETAILED DESCRIPTION OF THE INVENTION

Figure 5:
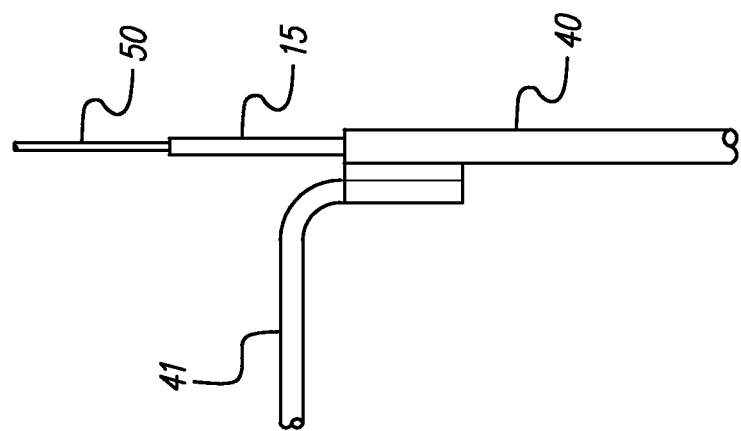
FIG. 5 shows, in accordance with the present invention, a view of the proximal end of the Advanced Bionics DBS lead and the proximal end of the microelectrode, which is partially inserted into the lead.

The following description is of the best mode presently contemplated for carrying out the invention. This description is not to be taken in a limiting sense, but is made merely for the purpose of describing the general principles of the invention. The scope of the invention should be determined with reference to the claims.

In an aspect of the present invention, a stimulation system is provided which includes an Advanced Bionics® DBS lead, a microelectrode and a detachable connector that can be attached to the microelectrode. The system may be used together using various existing MER methods. In addition one or more parts of the system are compatible for use with a wide variety of currently available MER recording systems.

The Advanced Bionics DBS lead has a lumen that runs axially from the distal end to the proximal end of the lead. The microelectrode, in accordance with the present invention, is designed without a permanent connector. In use, the microelectrode is operated with a removable (detachable) connector which may be attached and detached to the microelectrode at various points of a surgical procedure. Because the connector is detachable, the microelectrode may be inserted distal end first into the proximal end of the lumen in the DBS lead or, alternatively, the DBS lead may be inserted distal end first over the proximal end of a microelectrode.

FIG. 1 shows a conventional recording microelectrode 10 which may be inserted into the Advanced Bionics DBS lead 40. The conventional microelectrode 10 has a connector 20 which is permanently placed on the proximal end of the microelectrode. The distal end 30 of the microelectrode 10 is uninsulated and can make electrical contact with the surrounding tissue. The remainder of the microelectrode 10 may be insulated, but also excluding the small portion of the proximal end of the microelectrode, which may be electrically connected to recording circuitry. The Advanced Bionics DBS lead 40 has a connector portion 41 that is angled, preferably about 90 degrees from the remainder of the lead 40.

FIG. 2 shows a partial, expanded view of the conventional recording microelectrode 10 inserted into the lead 40, as shown in FIG. 1. Because the connector 20 is permanently connected, the microelectrode can only be inserted distal end first into the lumen at the proximal end of the DBS lead 40, as shown in FIG. 2.

Figure 3:
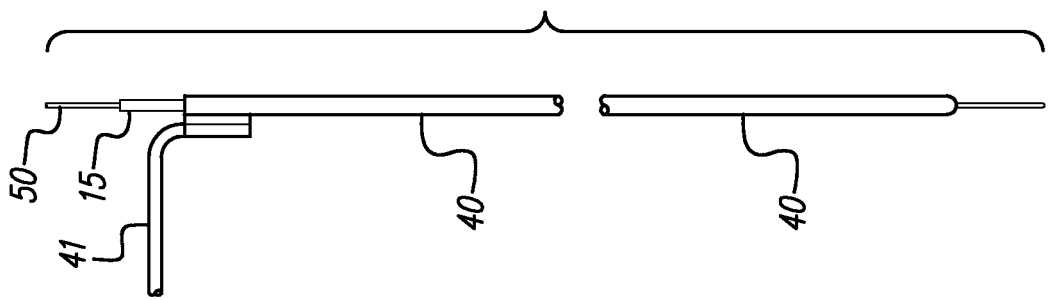
FIG. 3 shows, in accordance with the system of the present invention, the Advanced Bionics DBS lead inserted over the recording microelectrode (without a connector) of the present invention.

FIG. 3 shows, in accordance with the present invention, a system comprising a recording microelectrode 15 and an Advanced Bionics DBS stimulation lead 40 with a bent connector 41. The microelectrode 15 is shown inserted into the lumen of the Advanced Bionics DBS lead 40. The microelectrode does not have a fixed connector, but has both distal and proximal ends which are electrically conductive. A removable, conductive connector that is compatible with many currently available microdrives may be attached to the proximal conductive end 50 to insert the microelectrode 15 into a target tissue such as the brain. Preferably, the remainder of the microelectrode is covered with a thin exterior coating of insulation, for instance, polyimide.

Figure 4:
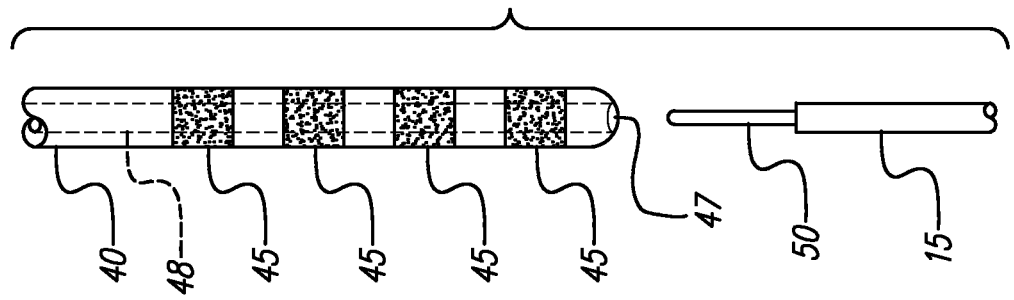
FIG. 4 shows, in accordance with the present invention, a view of the distal end of multi-electrode, Advanced Bionics DBS lead and the proximal end of the microelectrode (without a connector) of the present invention.

FIG. 4 shows a view of the distal end of the Advanced Bionics DBS lead 40 and the proximal conductive end 50 of the microelectrode 15, in accordance with the present invention. In this particular embodiment of the DBS lead four electrodes 45 are linearly placed in an "in-line" electrode array configuration. One of the four electrodes may be chosen as the active electrode to provide monopolar stimulation. To provide bipolar stimulation, at least two of the electrodes 45 may be selected. The quadrapole electrode arrangement further facilitates stimulation flexibility once the DBS lead is chronically placed, since the best electrode or electrode combination may be selected for optimal stimulation. The microelectrode 15 has a conductive proximal end 50. Because the microelectrode does not have a permanent connector attached to the proximal end 50, the microelectrode is dimensionally configured so that it may be inserted proximal end first into the lumen opening 47 at the distal tip of the DBS lead 40.

Advantageously, this allows the DBS lead to follow the microelectrode. For example, an introduction cannula may be placed into the brain. Then, using a microdrive, a microelectrode may be inserted through the introduction cannula with or without a connector attached to the microelectrode. Recordings are made until a suitable tissue site is found. Once a suitable site is found, the connector is detached and a DBS lead is inserted into the introduction cannula but slipped over the microelectrode. Once a proper position is found for the DBS lead, the microelectrode is withdrawn and the introduction cannula is also withdrawn, leaving the DBS lead permanently in place.

Alternatively, the DBS lead 40 may be placed into a target tissue, for instance the brain, followed later by the microelectrode through the lumen in the DBS lead, thereby effectively using the DBS lead as an introduction cannula and eliminating the use of at least one introduction cannula.

FIG. 5 shows the Advanced Bionics DBS lead 40 advanced over the microelectrode 15 until the proximal, connector end 50 of the microelectrode protrudes from the proximal end of the DBS lead. This position is achieved, for example, by first inserting the DBS lead 40 into a target tissue, and then inserting the microelectrode into the DBS lead 40, which may be used like an introduction cannula.

FIGS. 6A, 6B, 6C, 6D, 7A, 7B, 7C, 7D, 8A, 8B, 8C and 8D depict various views of removable connectors having different connection mechanisms for attaching and detaching the connector 60 to the microelectrode proximal end 50.

Figure 6B:
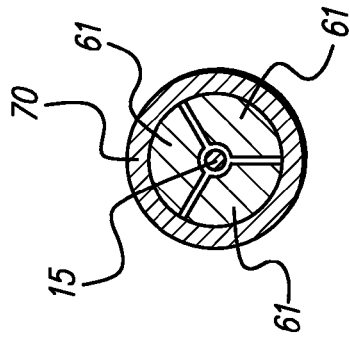
FIG. 6B shows a cross-sectional view of the connector and microelectrode depicted in FIG. 6A along lines 6B-6B.
Figure 6D:
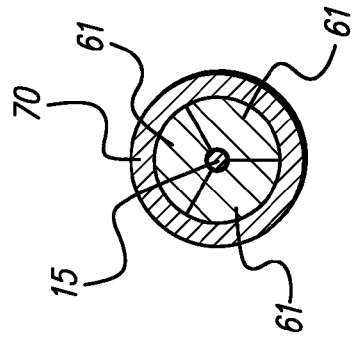
FIG. 6D shows a cross-sectional view of the connector and microelectrode depicted in FIG. 6C along lines 6D-6D.
Figure 6A:
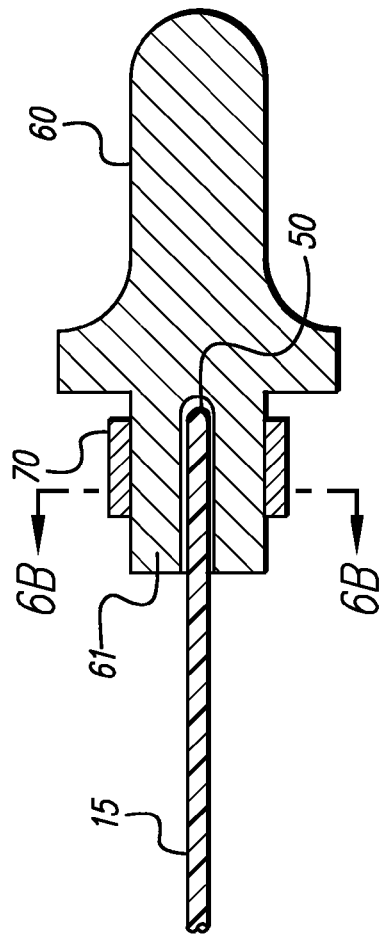
FIG. 6A shows, in accordance with the present invention, a longitudinal, cross-sectional view of the microelectrode and connector having a removable collet connection in an unlocked position.

FIG. 6A shows a longitudinal, cross-sectional view of the microelectrode 15 with connector 60 in an unlocked position. The connector 60 has a collet mechanism 70 for locking the microelectrode end 50 into the connector 60. The connector is made from a conductive material, such as a metal, which permits an extension lead linked to recording circuitry to be electrically connected to the connector and to the microelectrode.

FIG. 6B shows a cross-sectional view of the microelectrode 15 inserted within the connector 60 of the connector shown in FIG. 6A along the lines 6B-6B shown in FIG. 6A. FIG. 6B shows three "fingers" or segments 61 at the distal end of the connector 60.

Figure 6C:
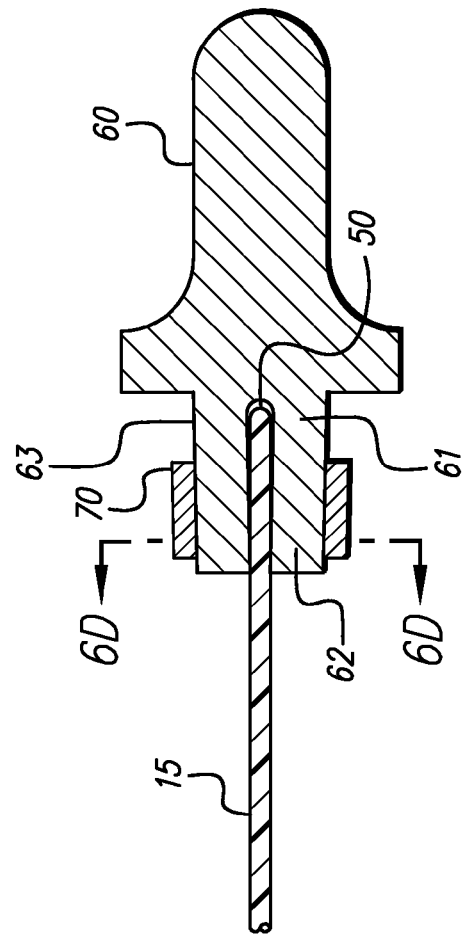
FIG. 6C shows a longitudinal, cross-sectional view of the connector and microelectrode shown in FIG. 6A, except in a locked position.

FIG. 6C shows another longitudinal, cross-sectional view of the microelectrode 15 and connector 60 shown in FIG. 6A except that collet ring 70 has been advanced forward toward the distal end 62 of the connector 60 thereby compressing the distal end 62 of the connector. The distal portion 62 of the connector 60 is configured so that as the collet 70 is advanced forward over the fingers 61, the fingers are compressed inwards towards the connector axis.

FIG. 6D shows a cross-sectional view of the microelectrode 15 inserted into the connector 60 along lines 6D-6D shown in FIG. 6C. The view shows the microelectrode 15 which is compressed by three finger sections 61 and thereby locking the microelectrode 15 into the connector 60. The three finger sections 61 are illustrative only and not limiting, as two, four or more finger sections may be used.

FIG. 7A shows a longitudinal, cross-sectional view of the microelectrode 15 with connector 60 in an unlocked position. The connector 60 has two ball bearings 80 as a connection mechanism.

FIG. 7B shows a cross-sectional view of the microelectrode inserted within the connector 60, viewed along lines 7B-7B shown in FIG. 7A. It can be seen that two springs 81 are placed to compress ball bearings 80 towards the center. The springs are lined up on either side of the connector axis.

FIG. 7C shows another longitudinal, cross-sectional view of the connector and microelectrode depicted in FIGS. 7A and 7B. In this depiction the microelectrode is fully inserted into the connector 60 with the two ball bearings 80 compressing the proximal end 50 of the microelectrode 15 thereby locking the microelectrode.

FIG. 7D shows a cross-sectional view of the connector 60 and microelectrode along lines 7D-7D shown in FIG. 7C. While the embodiment of the connector shown in FIGS. 7A, 7B, 7C and 7D show two ball bearings 80 placed in opposition to each other, it is also possible to use a ball bearing connector that has only one ball bearing 80 or more than two ball bearings. Furthermore, the proximal end 50 of the microelectrode 15 may have complementary surface depressions to help engage the ball bearings 80 of the connector 60 to the microelectrode.

FIG. 8A shows a longitudinal, cross-sectional view of the microelectrode 15 with connector 60 having a Bal Seal connection mechanism 90 (Bal Seal Engineering, Foothills Ranch, Calif.) with the connector in an unlocked position.

FIG. 8B shows a cross-sectional view of the connector 60 and the Bal Seal 90 along lines 8B-8B shown in FIG. 8A. The Bal Seal 90 is a coil that may be under tension and formed into a ring. When the proximal end of the microelectrode 50 is inserted inside the coil ring 90, it can compress the end of the microelectrode and lock it.

FIG. 8C shows another longitudinal, cross-sectional view of the microelectrode and connector with the Bal Seal, as in FIG. 8A, but with the microelectrode proximal end 50 locked into the connector with the Bal Seal 90.

FIG. 8D shows a cross-sectional view of the connector 60 and the ring-like Bal Seal 90 with the proximal end 50 of the microelectrode inserted into the connector 60 and locked by the Bal Seal.

FIG. 9A shows a side view of the proximal end of the microelectrode 15 with threads 101. The removable connector 60 has corresponding threads 100 within the connector 60 for accepting the threads 101 on the microelectrode.

FIG. 9B shows the microelectrode 15 and removable connector 60, as shown in FIG. 9A, but with the proximal end of the microelectrode 15 screwed into the connector 60 with corresponding inner threads 100. The microelectrode can be disconnected from the removable connector 60 by turning the connector, relative to the microelectrode.

FIG. 10A shows a side view of the proximal end of a microelectrode 15 and removable connector 60 having a channel 104 dimensioned to accept the proximal end of the microelectrode 15. In addition, the connector 60 has a threaded set screw hole 103 that communicates with the channel 104, which threaded set screw hole is dimensioned to accept the set screw 102.

FIG. 10B shows a cross-sectional view of the connector 60 and proximal end of microelectrode 15, as depicted in FIG. 10A. The set screw 102 is shown inserted in the threaded set screw hole 103. By turning the set screw in one direction, the tip of the set screw bears down mechanically on the proximal end of the microelectrode, thus locking the microelectrode with the removable connector 60. The set screw can be removed to release the microelectrode from the removable connector 60.

A collet mechanism, ball bearings and Bal Seal are only a few of the possible types of connection mechanisms that may be used with a removable connector. Other possible forms of connections that may be used to lock the microelectrode proximal end 50 into the connector 60 include: a threaded connection, a clip connection, a set screw connection, a spring loaded connection, a conductive adhesive connection and an interference fit.

In an aspect of the present invention, a system for recording and stimulating neural tissue is provided which includes a microelectrode 15 that can be used with a removable connector 60. In addition, the microelectrode and removable connector may be used with a DBS lead having a lumen that runs axially through the entire length of the lead. When the removable connector is detached, the microelectrode 15 is dimensioned to be completely passable through the lumen of the DBS lead 40. Because the connector may be removed and attached during any part of a recording and stimulating procedure, the microelectrode can be placed inside the DBS lead commencing at either the proximal or distal lumen openings of DBS lead 40.

As an integrated system, the DBS lead 40, the microelectrode 15 and the removable connector 60 can operate together to flexibly allow the recording microelectrode to be placed before, after, or concurrently with the placement of the DBS lead. Moreover, a recording microelectrode with a detachable connector permits the use of the Advanced Bionics DBS lead with all known MER methods and/or systems.

Figure 11:
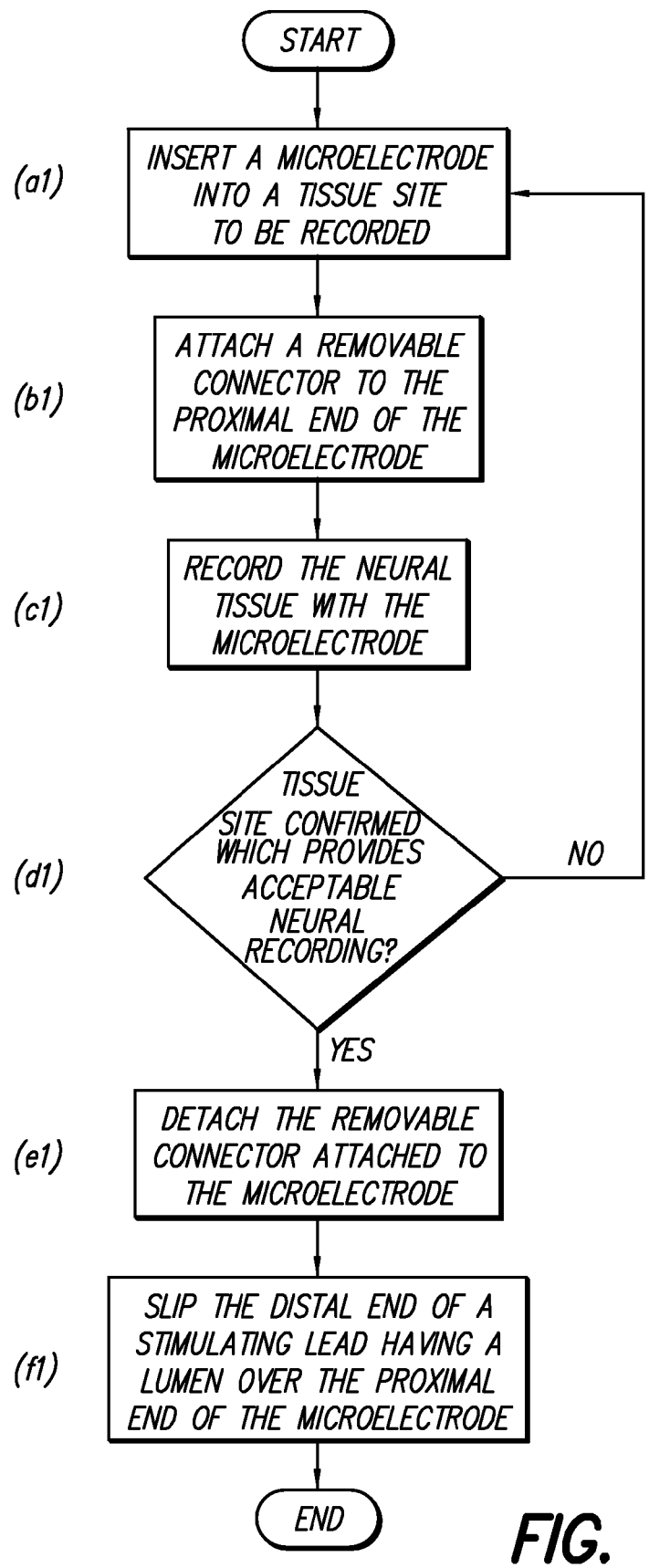
FIG. 11 shows a flow chart for an embodiment of a method of recording and stimulating neural tissue.

In another aspect of the present invention, there is provided a method for recording and stimulating neural tissue. In one embodiment of the method, the microelectrode may be first implanted into a tissue site and then followed by the DBS stimulating lead. As shown in FIG. 11, this embodiment of the method may comprise the following steps: (a1) inserting a microelectrode into a tissue site to be recorded; (b1) attaching a removable connector to the proximal end of the microelectrode; (c1) recording the neural tissue with the microelectrode; (d1) repeating the previous steps (a1), (b1) and (c1) until a tissue site is confirmed which provides an acceptable neural recording; (e1) if a tissue site is confirmed which provides acceptable neural recording, detaching the removable connector attached to the microelectrode; and (f1) slipping the distal end of a stimulating lead having a lumen over the proximal end of the microelectrode substantially covering the microelectrode, the lumen having a first opening at the proximal lead end and a second opening at the distal lead end. The microelectrode (without the connector attached) is configured and dimensioned to be completely passable through the lumen of the DBS lead, entering either at the first opening or the second opening. As an alternative embodiment of the method, step (b1) may be performed before step (a1).

The step (b1) of attaching a removable connector may be performed by using a connector having a connection mechanism selected from among the following types of connections: a threaded connection, a clip connection, a set screw connection, a spring loaded connection, a ball bearing connection, a Bal Seal connection, a collet connection and an interference fit.

As another embodiment of the method, the microelectrode and DBS stimulating lead may be inserted into the tissue site together as a system. The pre-insertion of the microelectrode into the DBS lead can beneficially contribute to the total stiffness of the microelectrode/stimulating lead combination and may thereby permit the combination to be inserted into tissue more than once without incurring irreversible lead deformation.

Figure 12:
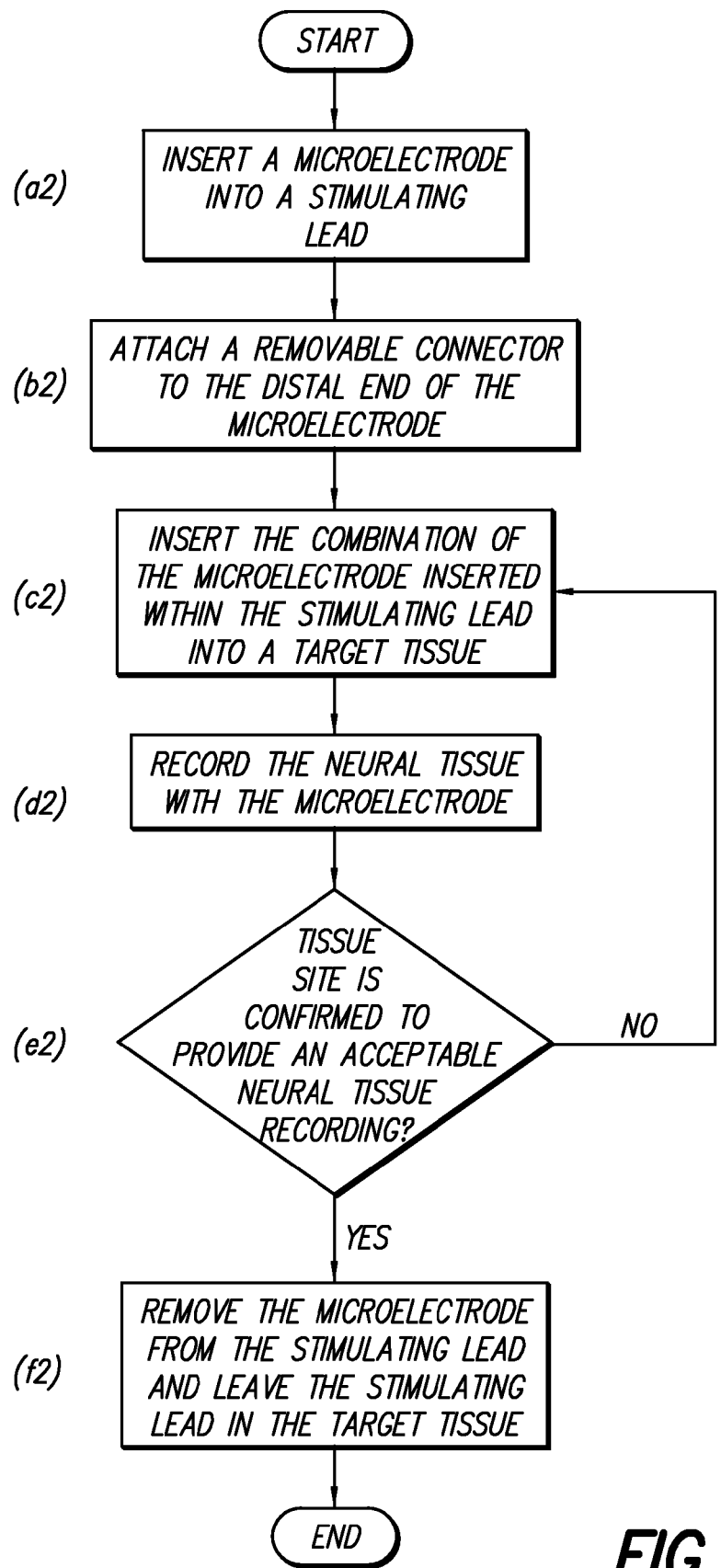
FIG. 12 shows a flow chart for another embodiment of a method of recording and stimulating neural tissue.

As shown in FIG. 12, this embodiment of the method may comprise: (a2) inserting a microelectrode into a stimulating lead, wherein the stimulating lead has a lumen with a first opening at the proximal lead end and a second opening at the distal lead end and wherein the microelectrode is configured and dimensioned to be completely passable through the lumen of the stimulating lead, entering either at the first opening or the second opening; (b2) attaching a removable connector to the distal end of the microelectrode; (c2) inserting the combination of microelectrode inserted within the stimulating lead into a target tissue, (d2) recording the neural tissue with the microelectrode; (e2) repeating the previous steps (c2) and (d2) until a tissue site is confirmed to provide an acceptable neural tissue recording; and (f2) if a tissue site is confirmed to provide an acceptable neural tissue recording, removing the microelectrode from the stimulating lead and leaving the stimulating lead in the target tissue. As an alternative embodiment, the step (b2) may occur before step (a2) or, as yet another embodiment, step (b2) may occur after step (c2).

Again, the step (b2) of attaching a removable connector may be performed by using a connector having a connection mechanism selected from among the following types of connections: a threaded connection, a clip connection, a set screw connection, a spring loaded connection, a ball bearing connection, a Bal Seal connection, a collet connection, and an interference fit.

Figure 13:
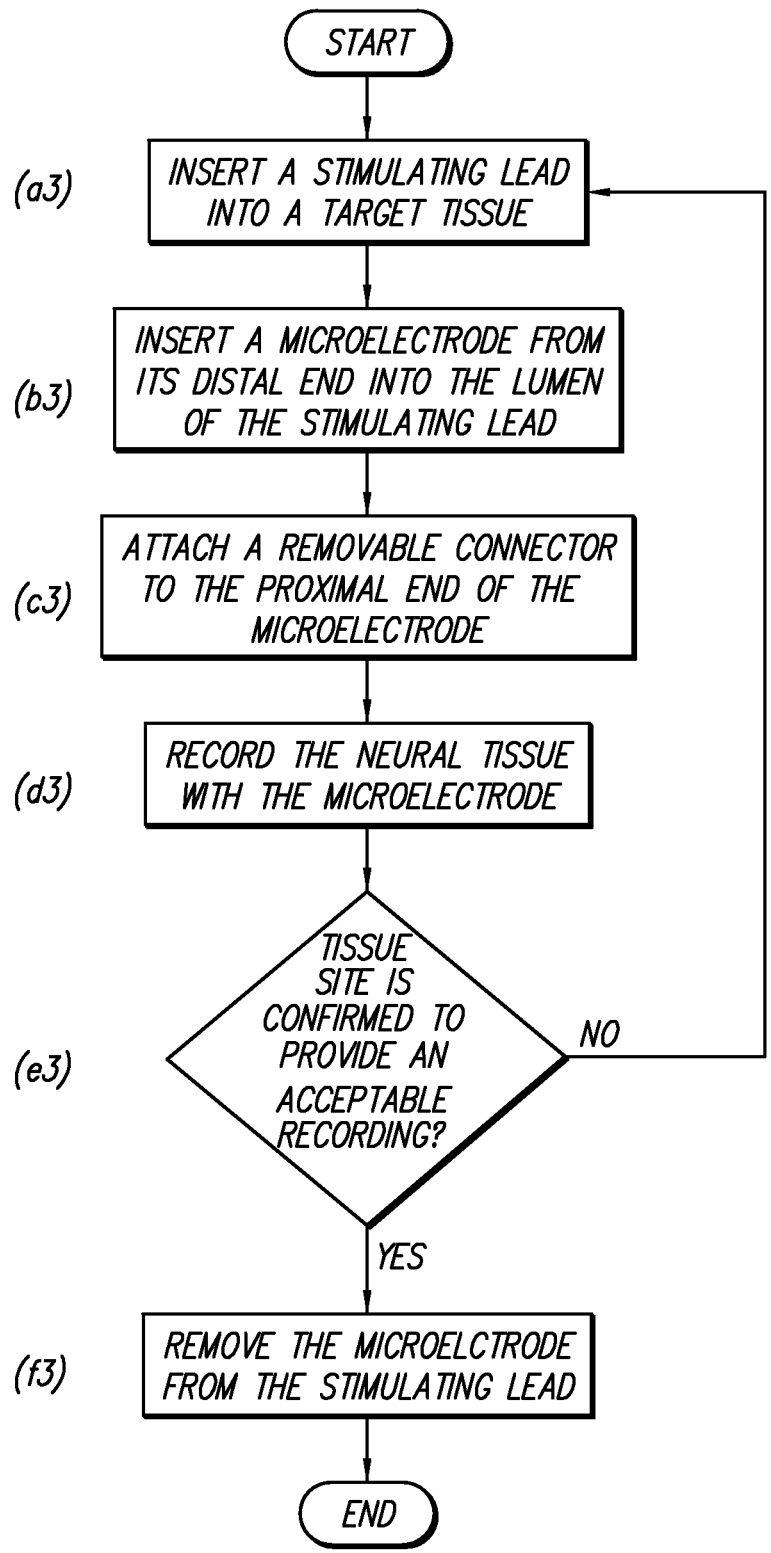
FIG. 13 shows a flow chart for yet another embodiment of a method of recording and stimulating neural tissue.

As a further embodiment of the method of recording and stimulating neural tissue, as shown in FIG. 13, the microelectrode may be placed into a DBS stimulating lead after it has been placed into the tissue. This embodiment comprises: (a3) inserting a stimulating lead into a target tissue, which stimulating lead has a lumen having a first opening at the proximal lead end and a second opening at the distal lead end; (b3) inserting a microelectrode from its distal end, into the lumen of the stimulating lead at its first opening, with the microelectrode configured and dimensioned to be completely passable through the lumen of the stimulating lead; (c3) attaching a removal connector to the proximal end of the microelectrode; (d3) recording the neural tissue with the microelectrode; (e3) repeating the previous steps until a site is confirmed to provide an acceptable recording; and (f3) if a tissue site is confirmed to provide an acceptable recording, removing the microelectrode from the stimulating lead.

Alternatively, in the above method, the step (c3) may occur before step (b3). In yet another alternative, the method above may include the step: stimulating the located tissue site with the stimulating lead, which step is performed between steps (e3) and (f3).

The step (c3) of attaching a removable connector may be accomplished by using a connector having a connection mechanism selected from the group consisting of a threaded connection, a clip connection, a set screw connection, a spring loaded connection, a ball bearing connection, a Bal Seal connection, a collet connection, and an interference fit.

In operation, the system of the Advanced Bionics DBS lead, microelectrode and removable connector can be used compatibly with a variety of procedures and microdrives as provided by the specific examples below.

Example 1

Microelectrode Placed Before the DBS Lead

An introduction cannula is inserted into the brain. The microelectrode is inserted through the cannula with the connector attached and cell recording is performed. When a promising tissue site is found, the connector is detached from the microelectrode and the Advanced Bionics DBS lead is inserted over the proximal end of the microelectrode and advanced into the brain until an electrode on the DBS lead is precisely at the located tissue site. Macrostimulation is performed with the DBS lead. If a physiologically acceptable response is obtained, then the microelectrode may be withdrawn and the DBS lead may be fixed for permanent implantation. If the physiological response is not acceptable, then the DBS lead and or microelectrode can be repositioned together or separately to locate a suitable tissue site.

Example 2

Microelectrode Placed Concurrently with DBS Lead

An introduction cannula is inserted into the brain. The microelectrode/Advanced Bionics DBS lead combination is inserted through the cannula with the connector attached to the microelectrode. The microelectrode is advanced slightly out of the distal end of the DBS lead and cell recording is performed. When a promising tissue site is found, the DBS lead is advanced over the distal end of the microelectrode until the electrodes on the DBS lead is precisely at the located tissue site. Macrostimulation is performed with the lead. If a physiologically acceptable response results, then the microelectrode may be withdrawn and the DBS lead may be fixed for permanent implantation. If the physiological response is not acceptable, then the DBS lead and or microelectrode can be repositioned such that microelectrode recording and/or macrostimulation can be performed until the DBS lead is properly positioned.

Example 3

Microelectrode Placed After the DBS Lead

An introduction cannula is inserted into the brain. An Advanced Bionics DBS lead has been inserted into the brain but the macrostimulation does not yield the desired physiological response. There is no microelectrode inserted inside the DBS lead. A microelectrode is then inserted through the DBS lead, and a microrecording is performed to locate a suitable tissue site. The lead position (depth) is then adjusted to coincide with the located site.

Example 4

"Five-At-A-Time" or Two Independent MER Microdrives

A physician using a "five-at-a-time" or two independent MER microdrives may perform the following procedure: conduct microelectrode recording(s) to determine the optimum target brain site based on the recordings, disconnect the removable connector from the microelectrode, insert the Advanced Bionics DBS lead over the proximal end of the microelectrode until the distal tip (electrode) of the DBS lead is over the distal end of the microelectrode, electrically connect the proximal portion of the DBS lead to stimulation circuits, conduct macrostimulation to confirm the stimulation efficacy of the site, remove the microelectrode and secure the DBS lead for permanent implantation. Many steps in the above procedure have been omitted, including notably, the steps involving placement of cannulas and insertion rods before placing a microelectrode or a DBS lead into the brain. If a DBS lead is implanted first, a separate cannula is not required for the microelectrode since it inserts directly into the lumen of the DBS lead. If a microelectrode is implanted first, the insertion cannula should be large enough to accommodate the DBS lead which will be inserted into the cannula but slipped over the microelectrode. In either case, one cannula is eliminated with the recording and stimulation system of the present invention because the microelectrode is designed to be insertable through the lumen of the DBS lead, as compared to using at least two cannulas in the conventional procedure, one for the microelectrode and another for the DBS lead.

Example 5

Single Tract Recording

The above-described procedure in Example 4 may be used when a single tract recording is performed. Alternatively, the method provided in Example 2 wherein the lead and recording microelectrode are inserted into the brain as one unit may be used. During placement of the DBS lead/microelectrode unit, the distal end of the microelectrode can be slightly recessed into the distal end of the DBS lead. The DBS lead/microelectrode unit can be advanced into the brain via an introduction cannula so that the distal tips of the lead/microelectrode are just above the desired target site. Once the unit is placed, the microelectrode distal tip can be extended out in small increments to make neural recordings and to localize an optimal stimulation site. Once the exact site is identified, the DBS lead can be advanced to cover the localized site. Macrostimulation can be performed to confirm the physiological efficacy of the site. If physiological efficacy is confirmed, the microelectrode can be withdrawn and the DBS lead secured for permanent implantation. If the target proves to be insufficient, the DBS lead/microelectrode can be withdrawn as a unit and reinserted as a unit into a different trajectory (tract). This procedure for electrode recording and macrostimulation is repeated until a suitable physiological response is obtained. Once the proper site is located, the microelectrode may be withdrawn and the DBS lead can be secured for chronic implantation.

While the microelectrode of the present invention is designed to be used in concert with a DBS lead having an axial lumen running from end to end, the microelectrode may also be used like a conventional microelectrode simply by attaching a connector.

In summary, the system of the Advanced Bionics DBS stimulating lead and microelectrode with a detachable connector provides the following advantages. The recording microelectrode is compatible with all known MER methods, including "five-at-a-time", two microdrives, single microelectrode, and multiple insertion methods. The detachable connector can be configured to have the requisite electrical and mechanical requirements for use with various MER electrical systems and microdrives and to be compatible with all output/inputs of known MER systems.

The stimulating/recording system of the DBS lead with a lumen extending entirely along its length and the microelectrode without a permanent connector attached, reduces surgical duration because it allows the microelectrode to also function as a guide or a stylet in placing the DBS lead. Only one cannula may be needed for both the DBS lead and microelectrode because of the unique system arrangement in which the microelectrode is insertable within the lumen of the DBS lead. Additionally, the microelectrode and DBS lead combination can be moved into a tract as a unit and, thus, function as a macroelectrode/stylet, eliminating the need for inserting a separate macroelectrode. Eliminating the use of a macroelectrode obviates the need for a separate introduction cannula for the macroelectrode. Thus, up to two introduction cannulas may be eliminated by using the recording and stimulation system of the present invention. Elimination of two cannulas and their attendant problems of misalignment can improve placement accuracy of the DBS lead which, in turn, may improve the therapy, prolong battery life and reduce scrapping of leads owing to missed placements. Also, fewer cannulas reduce surgical duration and risk of infection because there are fewer surgical steps needed and also because better accuracy of placement means fewer repeat insertions.

While the invention herein disclosed has been described by means of specific embodiments and applications thereof, numerous modifications and variations could be made thereto by those skilled in the art without departing from the scope of the invention set forth in the claims. By way of example, a DBS application has been discussed above. The lead system and methods described, however, may be used equally in other sites of the body other than the brain. In particular, the lead system of the present invention can be used in any application wherein a neural recording is first performed to identify a tissue site to achieve optimal neural stimulation.

What is claimed is:

1. A system for recording and stimulating excitable neural tissue, the system comprising:
    a microelectrode, configured and dimensioned to be completely passable through a lumen along the axial length of a stimulating lead, commencing from either a first opening or a second opening of the stimulating lead; and
    a removable connector for attaching and detaching the microelectrode from the stimulating lead, the removable connector including a locking mechanism.

2. The system of claim 1, wherein the locking mechanism is selected from the group consisting of a threaded connection, a set screw connection, a spring loaded connection, a Bal Seal connection, and a collet connection.

3. The system of claim 1, wherein the stimulation lead contains a conductor coil-defining the lumen.

4. The system of claim 1, wherein the stimulation lead has, as its proximal end, a connector portion that is angled from the remainder of the lead.

5. The system of claim 1, wherein the stimulation lead has an array of electrodes placed on the distal portion of the lead in an in-line placement.

6. The system of claim 1, wherein the stimulation lead has an array of electrodes placed on the distal portion of the lead in an in-line placement.

7. The system of claim 1, further comprising a recorder configured for recording the neural tissue with the microelectrode.

8. The system of claim 1, further comprising an insertion cannula configured for inserting the microelectrode into the neural tissue.

9. A system for recording and stimulating excitable neural tissue, the system comprising:
    a stimulation lead, having a lumen along its axial length, the lumen having two openings, a first opening at the proximal end of the lead, a second opening at the distal end of the lead;
    a microelectrode, configured and dimensioned to be completely passable through the lumen of the lead, commencing from either the first opening or the second opening of the lead; and
    a removable connector attached to the distal end of the microelectrode.

10. The system of claim 9, wherein the removable connector includes a locking mechanism.

11. The system of claim 10, wherein the locking mechanism is selected from the group consisting of a threaded connection, a set screw connection, a spring loaded connection, a Bal Seal connection, and a collet connection.

12. The system of claim 9, wherein the stimulation lead contains a conductor coil-defining the lumen.

13. The system of claim 9, wherein the stimulation lead has, as its proximal end, a connector portion that is angled from the remainder of the lead.

14. The system of claim 9, wherein the removable connector is configured to remove the microelectrode from the stimulation lead.

15. The system of claim 9, further comprising a recorder configured for recording the neural tissue with the microelectrode.

16. The system of claim 9, further comprising an insertion cannula configured for inserting the combination of microelectrode inserted within the stimulating lead into the neural tissue.

* * * * *